(12) United States Patent
Ahmad et al.

(10) Patent No.: US 7,851,419 B2
(45) Date of Patent: Dec. 14, 2010

(54) SUBSTANTIALLY ANHYDROUS SPRAYABLE PERSONAL LUBRICANT

(76) Inventors: Nawaz Ahmad, 26 Joseph Ct., Monmouth Junction, NJ (US) 08852; Cheng-Ji Cui, 3 Kentsdale Dr., Pennington, NJ (US) 08534; Michael Eknoian, 10 Ellsworth Dr., Warren, NJ (US) 07059; Russel Walters, 142 N. Bread St., Philadelphia, PA (US) 19106; Joseph James Librizzi, 19 Norz Dr., Hillsborough, NJ (US) 08844; H. Michael Moscherosch, 106 E. Oakland Ave., Doylestown, PA (US) 18901; Bryant Ison, 15 Pine Knoll Dr., Lawrenceville, NJ (US) 08648; Stephen J. Mohary, 111 Voorhees Ave., Pennington, NJ (US) 08534

( * ) Notice: Subject to any disclaimer, the term of this patent is extended or adjusted under 35 U.S.C. 154(b) by 75 days.

(21) Appl. No.: 11/403,520

(22) Filed: Apr. 13, 2006

(65) Prior Publication Data

US 2007/0059266 A1    Mar. 15, 2007

Related U.S. Application Data

(60) Provisional application No. 60/716,230, filed on Sep. 12, 2005.

(51) Int. Cl.
| | |
|---|---|
| A61K 8/34 | (2006.01) |
| A61K 8/86 | (2006.01) |
| C10M 171/02 | (2006.01) |
| C10M 171/04 | (2006.01) |
| C10M 171/06 | (2006.01) |
| C10M 161/00 | (2006.01) |
| C10M 145/28 | (2006.01) |
| C10M 129/08 | (2006.01) |

(52) U.S. Cl. .......... 508/219; 508/505; 508/583; 525/403; 424/70.11; 424/DIG. 14; 239/333

(58) Field of Classification Search .......... 508/219, 508/505, 583; 525/403; 424/70.11, DIG. 14; 239/333
See application file for complete search history.

(56) References Cited

U.S. PATENT DOCUMENTS

| | | | |
|---|---|---|---|
| 4,110,426 A | 8/1978 | Barnhurst et al. | |
| 4,233,876 A | 11/1980 | Leahy et al. | |
| 4,246,285 A * | 1/1981 | Van Duzee | 514/788 |

(Continued)

FOREIGN PATENT DOCUMENTS

EP    0 027 730 A2    4/1981

(Continued)

OTHER PUBLICATIONS

Neil H. Devlin. Loveland's move not so slick: [Final Edition]. Denver Post p. C.12. High Schools (Nov. 4, 2001). Retrieved Apr. 3, 2008, from ProQuest Newsstand database. (Document ID: 88345227).*

(Continued)

*Primary Examiner*—Randy Gulakowski
*Assistant Examiner*—Mike Dollinger

(57) ABSTRACT

This invention relates to personal lubricant compositions that are capable of being sprayed to a targeted area while maintaining lubricity.

5 Claims, 4 Drawing Sheets

U.S. PATENT DOCUMENTS

| | | |
|---|---|---|
| 4,347,237 A | 8/1982 | Evenstad et al. |
| 4,636,520 A | 1/1987 | Umio et al. |
| 4,720,507 A | 1/1988 | Wiebe |
| 4,863,725 A | 9/1989 | Deckner et al. |
| 4,950,475 A | 8/1990 | Vishnupad et al. |
| 4,981,686 A | 1/1991 | Hardy |
| 5,002,938 A | 3/1991 | Wang et al. |
| 5,208,031 A | 5/1993 | Kelly |
| 5,236,609 A | 8/1993 | Smith et al. |
| 5,270,032 A | 12/1993 | Pollock et al. |
| 5,349,149 A | 9/1994 | Shiraki et al. |
| 5,393,528 A | 2/1995 | Staah |
| 5,405,602 A * | 4/1995 | Simmons et al. ............... 424/47 |
| 5,512,289 A | 4/1996 | Tseng et al. |
| 5,513,629 A | 5/1996 | Johnson |
| 5,529,782 A | 6/1996 | Staab |
| 5,595,980 A | 1/1997 | Brode et al. |
| 5,599,551 A | 2/1997 | Kelly |
| 5,658,583 A | 8/1997 | Zhang et al. |
| 5,696,164 A | 12/1997 | Sun et al. |
| 5,709,849 A | 1/1998 | Ito et al. |
| 5,750,122 A * | 5/1998 | Evans et al. ................. 424/401 |
| 5,840,744 A | 11/1998 | Borgman |
| 5,885,591 A | 3/1999 | Ahmad et al. |
| 5,895,658 A | 4/1999 | Fossel |
| 5,902,593 A | 5/1999 | Kent et al. |
| 5,976,561 A | 11/1999 | Kent et al. |
| 5,980,875 A | 11/1999 | Mousa |
| 5,980,924 A | 11/1999 | Yamazaki et al. |
| 6,007,846 A | 12/1999 | Klar |
| 6,013,270 A | 1/2000 | Hargraves et al. |
| 6,019,782 A | 2/2000 | Davis et al. |
| 6,060,077 A | 5/2000 | Meignant |
| 6,139,848 A | 10/2000 | Ahmad et al. |
| 6,143,329 A * | 11/2000 | Kim ........................... 424/489 |
| 6,153,208 A | 11/2000 | McAtee et al. |
| 6,171,604 B1 | 1/2001 | Mousa |
| 6,190,680 B1 | 2/2001 | Sakurada et al. |
| 6,221,814 B1 | 4/2001 | Kaburagi et al. |
| 6,303,108 B1 | 10/2001 | Boulier et al. |
| 6,338,855 B1 | 1/2002 | Albacarys et al. |
| 6,432,415 B1 * | 8/2002 | Osborne et al. ............. 424/400 |
| 6,531,171 B2 | 3/2003 | Armand et al. |
| 6,641,825 B2 | 11/2003 | Scholz et al. |
| 6,664,296 B1 | 12/2003 | Meignant |
| 6,706,674 B2 | 3/2004 | Cincotta |
| 6,756,520 B1 * | 6/2004 | Krzysik et al. ............... 604/360 |
| 7,005,408 B2 * | 2/2006 | Ahmad et al. ............... 508/219 |
| 7,417,013 B2 * | 8/2008 | Ahmad et al. ............... 508/463 |
| 2002/0013304 A1 | 1/2002 | Wilson et al. |
| 2002/0038823 A1 * | 4/2002 | Tardif ......................... 239/333 |
| 2002/0103414 A1 | 8/2002 | Harrison et al. |
| 2003/0013675 A1 * | 1/2003 | Yeadon et al. ................ 514/46 |
| 2003/0092754 A1 | 5/2003 | Nishimuta et al. |
| 2003/0114522 A1 | 6/2003 | Brogan et al. |
| 2003/0191180 A1 * | 10/2003 | Ross .......................... 514/454 |
| 2003/0211161 A1 | 11/2003 | Ahmad |
| 2003/0232090 A1 | 12/2003 | Ahmad |
| 2004/0138074 A1 | 7/2004 | Ahmad |
| 2004/0167039 A1 | 8/2004 | Ahmad |
| 2004/0185065 A1 | 9/2004 | Ahmad |
| 2005/0042248 A1 | 2/2005 | Ahmad |
| 2005/0042249 A1 | 2/2005 | Ahmad |
| 2006/0094608 A1 | 5/2006 | Ahmad |
| 2007/0059250 A1 * | 3/2007 | Ahmad et al. ................. 424/45 |

FOREIGN PATENT DOCUMENTS

| | | |
|---|---|---|
| EP | 0 404 376 A2 | 12/1990 |
| EP | 0 581 581 A2 | 2/1994 |
| EP | 0 966 956 B1 | 12/1999 |
| GB | 1345510 A * | 1/1973 |
| NZ | 235054 A | 11/1992 |
| RU | 98108031 A | 4/1997 |
| RU | 2155582 C2 | 9/2000 |
| WO | WO 99/29301 A | 6/1999 |
| WO | WO 01/05400 A1 | 1/2001 |
| WO | WO 01/64176 A1 | 9/2001 |
| WO | WO 02/087570 A1 | 11/2002 |
| WO | WO 03/092652 A | 11/2003 |
| WO | WO 2005/000324 A | 1/2005 |

OTHER PUBLICATIONS

I Can'T Believe Its Not Butter!TM. Jun. 3, 2004. Internet Archive Wayback Machine. http://web.archive.org/web/20040603161310/www.tasteyoulove.com/products.asp?section=products/spray.*

PAM4You. Apr. 7, 2008. Note reference to use of PAM "for over 45 years". http://www.pam4you.com/pages/index_flash.jsp.*

Biochemicals: Ultrapure: Polyethylene Glycol 400. Product 19957. CAS # 25322-68-3. USB Corporation. http://www.usbweb.com/category.asp?cat=bio&id=19957.*

* cited by examiner

SUBSTANTIALLY ANHYDROUS SPRAYABLE PERSONAL LUBRICANT

This application is a non-provisional application based upon Provisional Patent Application Serial No. 60/716,230 filed Sep. 12, 2005 and hereby incorporates herein the subject matter of that application.

FIELD OF THE INVENTION

The present invention relates to a composition useful for personal lubrication during intimate contact that is applied by atomization. In particular, the compositions are sprayed onto a defined body target area.

BACKGROUND OF THE INVENTION

Personal lubrications for intimate contact are well known. Typically, personal lubricants are marketed as liquids, jellies, gels or suppositories. Examples of such products include K-Y® Jelly, Astroglide®, K-Y® Liquid, K-Y® Ultragel™. More recently K-Y® Warming Liquid was introduced to the marketplace. K-Y® Warming Liquid is a water soluble, anhydrous composition that warms on contact while providing lubrication.

Most of the commercially available personal lubricant products are used by first applying to the hand or fingers of the user and then to the intimate area. This can be undesirable and messy. Additionally, some individuals are adverse to applying a personal lubricant directly to the genital regions.

One method to deliver a liquid hands-free is through spraying. Spraying a composition can be accomplished in one or more ways. For example, there exist two products from Durex sold in a spray pump dispenser. When dispensed, the products, Play Warmer Lubricant and Play Tingling Lubricant, come out of the nozzle in a viscous stream or single line, the direction of which is controlled by gravitational force. The stream of lubricant does not extend beyond a short distance, making it difficult to dispense to a specific target area. Additionally, the stream that is sprayed out is not atomized and does not result in a relatively uniform layer of lubricant over a target area. Furthermore, the pumping mechanism does not change the properties of the composition when dispensed.

There are also commercially available oils, lubricants and food products that reside in spray containers that utilize atomization. For example, WD-40®, a household lubricant containing petroleum distillates (commercially available from the WD-40 Company of California), is an aerosol containing carbon dioxide propellant that can be sprayed in a wide spray pattern. This product also has a straw-type attachment, which allows it to be delivered to a specific site.

Another spray pump dispensing device that is capable of atomizing a composition contains a swirl chamber that breaks up the composition into minute particles or into a fine spray, which is then expelled. Examples of products that may be atomized are olive oil sprays, artificial oleo spreads, hair care products, mechanical lock lubricants, sun care skin products and massage oils. Other products which require both sprayability and lubricity may be conveniently made in accordance with the compositions and methods of this invention, for example, hair sprays or skin moisturizers.

However, not all liquids are capable of being sprayed. This has been a particular challenge in the area of personal lubricants. Typically, personal lubricants have a high viscosity, resulting in a much thicker solution than is generally thought of as being capable of being sprayed. Additionally, some personal lubricants are not liquids but are gels and jellies.

Lowering the viscosity of such personal lubricant compositions by diluting the composition with liquid, however, generally causes the composition to lose lubricity.

Therefore, there exists a need for a sprayable composition for personal lubrication use that results in a controlled delivery to a defined target area.

SUMMARY OF THE INVENTION

Figure 1:
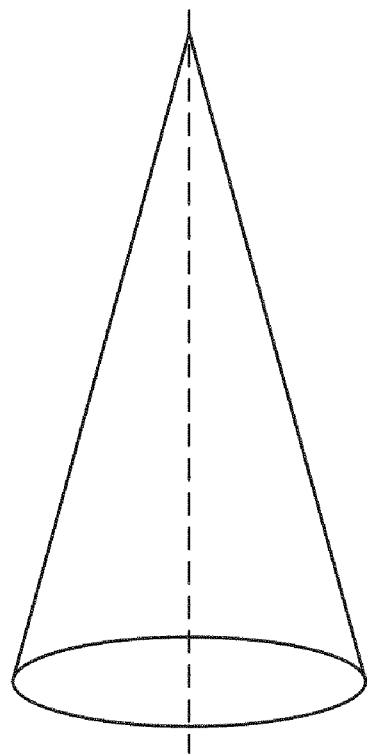
FIG. 1 illustrates the conical spray pattern of compositions of this invention.
Figure 2:
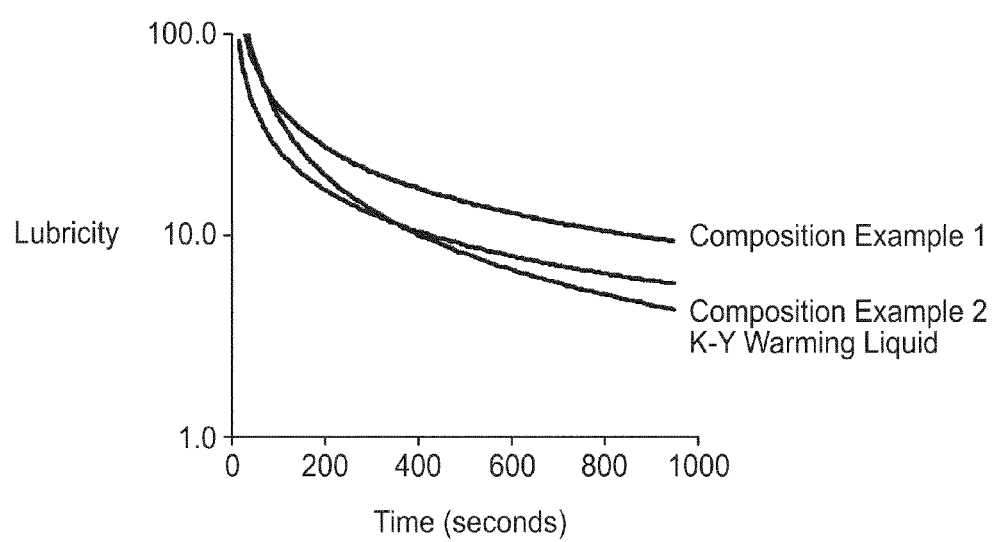
FIG. 2 is a graph illustrating a comparison of lubricity of Composition Example 1 and Example 2 of the invention with K-Y® Warming Liquid.
Figure 3:
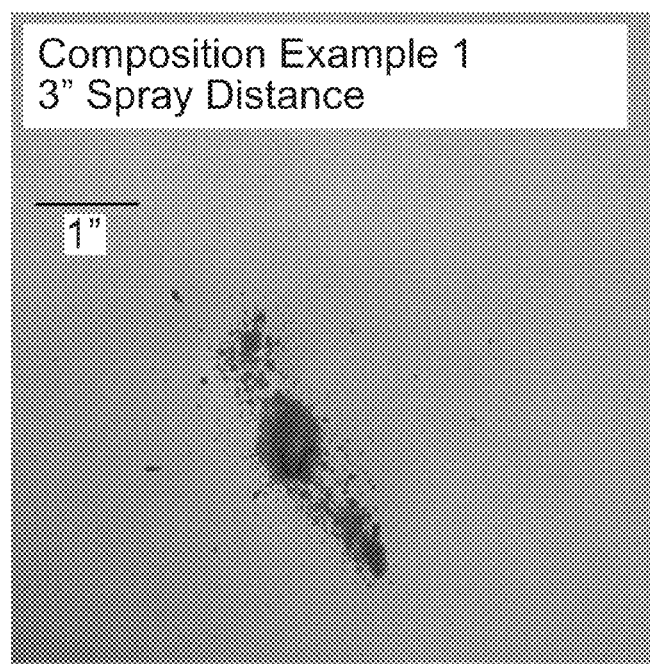
FIG. 3 is a photograph of a preferred spray pattern and spray area covered by the composition 1 of the invention when it is applied from a distance of 3 inches.
Figure 4:
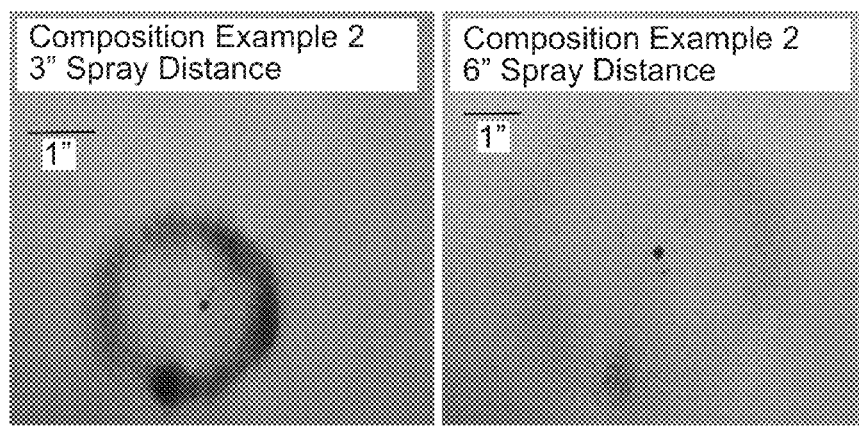
FIG. 4 is a photograph of a preferred spray pattern and spray area covered by Example 2 of the invention from a distance of 6 inches and 3 inches.

We have discovered that, unexpectedly, imparting certain physical characteristics to personal lubricant compositions endows them with the capability of being sprayable while retaining sufficient lubricity to be used as a personal lubricant.

Preferably, the personal lubricant compositions of this invention have a lubricity of at least about 8 and exhibit lubricious behavior after spraying and when applied to a surface.

DETAILED DESCRIPTION OF THE INVENTION

As used herein, the term "spray stream" refers to a spray pattern wherein the composition is disposed within approximately a single line. The line may initially be straight, but may be caused to curve in accordance with gravitational force exerted upon the stream. The composition does not radiate outward from the line.

As used herein, the terms "target sprays," "target sprayable" are defined to mean that the composition may be dispensed from a nozzle in a conical-shaped pattern when viewed from the side. This excludes all types of sprays that deliver in a stream. In one embodiment, the target spray dispenses from the nozzle orifice such that the droplets radiate outward. If a central axis were to be drawn perpendicular from the nozzle orifice, the droplets would radiate outward about such axis at an angle greater than zero degrees but less than 180 degrees. One example of this pattern is set forth in FIG. 1.

The target spray preferably results in a filled patterns upon the target area. As used herein, the term "filled pattern" means that the composition of the target spray is distributed and coats the at least a portion of the defined target area and not just the outer edges, which results in a "halo" appearance. While the defined target area need not have a defined shape, it is possible by optimizing the sprayer and spray nozzle to have a defined target area of, for example, a diamond. Other embodiments such as circles, ovals and the like are possible.

The intent of coating the defined target area with a filled spray pattern is to ensure that the application of the composition may be controlled and applied to a desired target area. This would prevent the composition from being applied to an area that is not desired by the individual using the product, i.e., bedding, clothes, flooring, furniture or other portions of anatomy.

The term "mist" is used herein to refer to a spray pattern that does not have clearly defined outer boundaries.

Unexpectedly, the compositions of this invention have relatively high lubricity even after having been sprayed. In one embodiment, the defined target area has an area of about 0.75 to about 3 square inches. In another embodiment, the defined circular target area is 0.5 to about 2.5 square inches.

Preferably, the viscosity of the compositions of this invention should be less than about 250 cps on a Brookfield Viscometer LVT-2 and 6 rpm. A higher viscosity composition would be too viscous to be capable of spraying.

In order to obtain the filled pattern, it may be necessary to spray the composition from a predetermined distance from the target area. For example, in one embodiment, a user may position the spray nozzle approximately 1.5 to 4 inches from the body. In another embodiment, the user may hold the spray nozzle approximately 2 to 3 inches from the body. Additionally, the spray container may be configured to be sprayed in an upright manner or upside down. For example, a female user may prefer to invert the container while dispensing the contents to her perineal area more conveniently.

As used herein, the phrase personal lubrications means those types of compositions that supply lubrication during personal or sexual relations. The personal lubrication of this invention may be applied to the vagina, vaginal area, perineum, anal area, penis, or oral cavity. In the event that manual stimulation or penetration is desired, the composition may be applied to the hands or fingers. The composition may also be applied to devices such as medical devices, gloves, or sexually-related devices such as vibrators, sexual aids, and the like. The personal lubricant may also contain flavors or fragrances to impart sensory variety to the composition.

The composition utilized in this invention may be any composition that is sprayable and lubricating in accordance with this invention. In another embodiment, the sprayable composition may be an anhydrous composition.

If the compositions of this invention are to be utilized in conjunction with a latex condom, however, they should not contain oil or other petroleum products or other components that would tend to degrade such condoms.

The compositions of this invention may be substantially anhydrous, preferably containing less than about 20% water, more preferably containing less than about 5% water and, most preferably, containing less than about 3% water. In one embodiment, the composition may contain at least one polyhydric alcohol, and more preferably, two polyhydric alcohols. Preferably the polyhydric alcohol portion of the compositions of this invention are one or more polyhydric alcohols such as alkylene glycols and others selected from the following group: glycerin, propylene glycol, butylene glycol, hexalene glycol or polyethylene glycol of various molecular weight and the like and/or combination thereof. More preferably, the compositions of this invention contain a polyethylene glycol; most preferably, the polyethylene glycol may be selected from the range of polyethylene glycol 300 to about polyethylene glycol 2000. More preferably, the range should be from about polyethylene glycol 400 and about polyethylene glycol 1450. The compositions of this invention should contain polyhydric alcohols in an amount from about 80% to about 98% by weight of the composition.

More preferably, the compositions of this invention contain at least two polyhydric alcohols. Even more preferably, the compositions of this contain propylene glycol and at least one polyethylene glycol. Most preferably, two polyethylene glycols are present having different numbers of ethylene glycol units. For example, the compositions of this invention preferably contain propylene glycol and polyethylene glycol 400 or polyethylene glycol 1000; preferably they may contain propylene glycol and PEG 400 as well as PEG 1000 or PEG 1450. Preferably, polyethylene glycol of less than about 2000 ethylene glycol units is used as higher molecular weight ingredients tend to cause the composition to solidify. Lower molecular weight ingredients tend to permit the composition to be sprayed as they have a lower viscosity.

The compositions may be self-preserving and may not require a preservative. However, a preservative may be added to impart an additional guarantee against microbial growth. A preservative may be selected from preservatives known to those of skill in the art, including, but not limited to, one or more of the following: methylparaben, benzoic acid, sorbic acid, gallic acid, propylparaben or the like. The preservative may be present in the compositions of this invention in an amount from about 0.01% to about 0.75% by weight of the composition.

Other ingredients which may be included in the compositions of this invention preferably include those set forth in Such warming personal lubricants are described in, for example, U.S. Pat. No. 7,005,408 as well as in U.S. patent applications Ser. No. 10/390,511 filed Mar. 17, 2003, No. 10/389,871, filed Mar. 17, 2003, No. 10/696,939, filed Oct. 30, 2003, No. 10/697,353, filed Oct. 30, 2003, No. 10/697, 838, Oct. 30, 2003, No. 10/847,082, May 17, 2004 and No. 10/847,083, filed May 17, 2004, which are hereby incorporated herein by reference and in copending patent applications Ser. Nos. 11/403,592 and 11/403,523 the subject matter of which is incorporated herein by reference, including antioxidants such as ascorbic acid, butylated hydroxyanisole and tocopherol.

The compositions may also contain an ester. More preferably, the ester is a fatty acid ester. Most preferably, the ester may include, but is not limited to: isopropyl stearate, isopropyl myristate, isopropyl palmitate, isopropyl laurate and the like. Most preferably, the ester is isopropyl myristate.

The polyhydric alcohols used in the compositions of this invention are theorized to be useful as warming and heat-generating agents. The ester, preferably a fatty acid ester, functions as an emollient and lubricant. The compositions of this invention are unique in that they lubricate, warm and soothe the tissues of the user, especially the oral and vaginal mucous membranes, without conveying a feeling of cold. Moreover, they are smooth and lubricating.

The anhydrous sprayable compositions of this invention may be a liquid or a semi-solid.

As defined earlier, the sprayable composition of this invention may be used as personal lubricants and/or moisturizers. As such, the anhydrous compositions of the present invention may convey a feeling of warmth when sprayed onto the user. The feeling of warmth generated by the compositions of this invention is soothing to the skin or mucous membranes where they are applied. The compositions of this invention may also possess a sweet and pleasant taste, which is of particular benefit when these compositions are used orally. Such personal lubricants are useful in facilitating sexual intercourse and serve to enhance intimacy in sexual activities.

Yet other embodiments of the compositions of this invention are compositions that may include local anesthetics. The local anesthetics may preferably include, but are not limited to, benzocaine, lidocaine, dibucaine, benzyl alcohol, camphor, resorcinol, menthol and diphenylhydramine hydrochloride and the like.

Compositions of the invention may also include plant extracts such as aloe, witch hazel, chamomile, hydrogenated soy oil and colloidal oatmeal, vitamins such as vitamin A, D or E and corticosteroids such as hydrocortisone acetate.

Lubricity

The compositions of the present invention provide personal lubrication. Personal lubricants substantially prevent irritation, which may result due to friction during sexual activity. As an example, some post-menopausal women find sexual intercourse painful due to dryness of the vagina. Such a condition may also be the result of other origins including female sexual dysfunction. The use of a personal lubricant helps to overcome this condition.

Lubricity may be measured using the following test method known herein as the "Ahmad Procedure" which was described in U.S Pat. No. 6,139,848. Briefly, the test method measures the amount of force required to move one surface relative to another while under weight pressure (the two surfaces being horizontal to each other). A weight or pressure can be applied on the upper moving surface. The test composition, in this case, the test lubricants, work by reducing the friction between the two surfaces. From this force and weight, a coefficient of friction value for a lubricant can be calculated. The coefficient of friction is inversely proportional to the lubricity of a product and is known as "relative lubricity". Relative lubricity can be calculated from the coefficient of friction data by dividing the numeral one by the corresponding coefficient of friction value.

An instrument, namely Coefficient of Sliding Friction Rig adapted to a Texture Analyzer, marketed by Texture Technologies Corp., 18 Fairview Road, Scarsdale, N.Y. was used for determining relative lubricity of several lubricant products in comparison with that of the compositions of this invention. The equipment contains a platform having a friction sledge attached to a load cell which is constrained to slide across the platform over which a test sample is applied. Load is provided by a 430 g precision weight positioned centrally over the sledge. This arrangement offers the advantage of measuring coefficient of sliding friction in both directions such that data for the "push" and the "pull" phases of the test can be generated over a fixed period of time. For the examples set forth below, it was possible to generate coefficient of friction data for an extended period of five (5) minutes. In making the measurements for the examples, a non-lubricated condom was mounted over the sledge, a thin film of the lubricant sample was applied over the fixed platform and coefficient of sliding friction readings were recorded over a five-minute period while the friction sledge went back and forth from the starting point. The coefficient of friction data, therefore, has negative (−) sign during the "push" phase and positive (+) sign during the "pull" phase of the experiment. The coefficient of friction data for the baseline, with no product applied to the condom was also generated for comparison. Texture Analyzer TA-XT2I (SID 41) was utilized for the test, having a Plexi-glas™ plate 3"×4"×⅜" in size, a 430 g weight and a 6.0 mil Bird Applicator. The substrate used was a polyethylene/foil liner and a Trojans® non-lubricated condom. The texture analyzer settings were as follows: Test Mode and Option, Measure Force In tension, Cycle Until Count, Trigger, Type-Button, Stop Plot at—Trigger Return, Brea—Detect off, level. The pre-test speed was 0 mm/s, the test speed was 2.0 mm/s, the post test speed was 0.0 mm/s and the distance traveled was 40.0 mm. The test was run for 300 seconds. The PE/foil liner was glued to the aluminum base or platform of the Texture Analyzer. The Plexi-glas™ sled was covered with the condom, a 6.0 mil film of test product was cast onto the liner and the 430 g weight placed on the center of the sled.

Preferably, the lubricity range for the compositions of this invention as determined using the Ahamd procedure should be at least about 8 for the duration of between about 100 and about 900 seconds, more preferably, more than about 30 for the duration of between about 100 and about 900 seconds.

Viscosity

In order for the composition to be sprayable, the composition must have a certain viscosity, which allows the composition to be sprayed. It has been found that while achieving the appropriate viscosity, maintaining lubricity is equally important.

The composition may be sprayed through a pump spray or a spray valve or an actuator adapted to a container. The compositions of this invention may also be dispensed using an aerosol spray device, preferably one that does not employ propellant in the spray composition.

The viscosity must be such that the composition can be drawn into and up through the delivery mechanism of the sprayer. This may include a dip tube, into an actuator and a spray orifice. In one embodiment, the viscosity of the composition is in the range of less than about 250 cps as measured by a Brookfield Instrument with an RVT spindle at a speed of 20 rpm at 25° C..

Spray Mechanisms

In one embodiment, the spray mechanism useful with this invention is a spray pump-actuator combination.

In spray pumps having a swirl chamber, the composition is typically drawn up into the chamber by a dip tube. Once inside the swirl chamber, the composition breaks up into minute particles or to a fine spray, which is then expelled.

Once the spray pump has been primed, the composition is delivered to the defined target area in predetermined amounts. In one embodiment, the pump required at least two strokes to prime. In another embodiment, the pump required at least three strokes to prime. During priming, the composition is drawn up the dip tube, into the swirl chamber, through the actuator and eventually expelled. In one embodiment, the spray pump delivers 120 to 160 μL of composition per a single stroke into the defined target area.

In order to be sprayable, the compositions of this invention should be capable of being atomized into particles having a size distribution as follows, given for the $10^{th}$, $50^{th}$, and $90^{th}$ percentiles:

| | Particle Size (μm) | | |
|---|---|---|---|
| Distance | D[v, 0.1] | D[v, 0.5] | D[v, 0.9] |
| 3" | 417 | 40 | 119 |
| 6" | 235 | 40 | 81 |

Preferably, particle size at 3" should be at least about 400 μm in the $10^{th}$ percentile, at least about 40 μm in the $50^{th}$ percentile and at least about 100 μm in the $90^{th}$ percentile and at 6", at least about 200 μm in the $10^{th}$ percentile, at least about 40 μm in the $50^{th}$ percentile and at least about 75 μm in the $90^{th}$ percentile.

In one embodiment, the spray pump may be a two-way pump, that is, the composition contained within the pump can be dispensed from an upright or inverted configuration such that the user can spray "upside down".

Preferably, the compositions and methods of this invention enable the compositions to be dispensed from a location remote from the target area with minimal dispersion to undesired areas. For example, the compositions may be sprayed at a target area with reasonable accuracy from a distance of from at least about three to at least about twelve inches or further.

The compositions of this invention are preferably propelled out of the dispenser at a pressure which is high enough to counteract gravitational force. This preferably occurs whether or not the compositions of this invention are aerosolized by the pumping device utilized to dispense them. The compositions of this invention may be propelled from a pump spray or an aerosol spray, which dispenses a continuous spray rather than a "batch" spray, depending upon whether the pump must be primed. The methods of this invention also provide the user with a controlled dose of composition delivered to a target area if the compositions are dispensed using a primed pump.

The methods of this invention include methods of applying personal lubricants by placing a composition of this invention in a pump spray mechanism and dispensing the composition to a target area from a distance of at least three inches. Such compositions may be applied to mucous membranes, including oral, nasal, or vaginal membranes. The method of this invention may also include applying the compositions of this invention to external genitalia prior to or during intercourse in order to provide personal lubrication during intercourse.

The following examples serve to illustrate the compositions and methods of this invention. However, they are not presented in order to limit the scope of the invention in any way.

Inventive Examples 1-4 may be prepared as follows:

The compositions were prepared by adding propylene glycol and polyethylene glycol 400 in a container and mixing them using a lightening mixer. The compositions containing polyethylene glycol 1000 were heated to a temperature of 40-50° C. and mixed using a mixer.

| Ingredient | % w/w |
|---|---|
| Inventive Example 1 | |
| Propylene Glycol | 75.00 |
| Polyethylene glycol 400 | 25.00 |
| Total | 100.00 |
| Inventive Example 2 | |
| Propylene Glycol | 90.00 |
| Polyethylene glycol 400 | 10.00 |
| Total | 100.00 |
| Inventive Example 3 | |
| Propylene Glycol | 60.00 |
| Polyethylene glycol 400 | 40.00 |
| Total | 100.00 |
| Inventive Example 4 | |
| Propylene Glycol | 95.00 |
| Polyethylene glycol 1000 | 5.00 |
| Inventive Example 5 | |
| Propylene Glycol | 50.00 |
| Polyethylene glycol 400 | 25.00 |
| Polyethylene glycol 1000 | 25.00 |
| Inventive Example 6 | |
| Propylene Glycol | 50.00 |

-continued

| Ingredient | % w/w |
|---|---|
| Polyethylene glycol 400 | 25.00 |
| Polyethylene glycol 1450 | 25.00 |
| Inventive Example 7 | |
| Propylene Glycol | 25.00 |
| Polyethylene glycol 400 | 50.00 |
| Polyethylene glycol 1000 | 25.00 |
| Inventive Example 8 | |
| Propylene Glycol | 25.00 |
| Polyethylene glycol 400 | 50.00 |
| Polyethylene glycol 1450 | 25.00 |

Comparative Examples 1-3

Relative lubricity data presented in FIG. 1 was calculated from the coefficient of friction data generated using the Ahmad Method as described above. The lubricants tested were the compositions as detailed in Inventive Examples 1 and 2 and K-Y® Warming Liquid, a commercially available product. As shown, Example 1 overall showed higher lubricity that continued for a longer period of time than K-Y® Warming Liquid. Additionally, Example 2 exhibited similar lubricity to K-Y® Warming Liquid from 0 to 400 seconds at which time, Example 2 maintained lubricity while K-Y® Warming Liquid decreased.

Table 1 shows the sprayablity of commercial products and Examples 1 and 2 as described above.

| Sample | Form | Sprayable Composition* (yes or no) |
|---|---|---|
| Commercial Product 1 | Liquid | No |
| Commercial Product 2 | Gel | No |
| Commercial Product 3 | Liquid | No |
| Commercial Product 4 | Liquid | No |
| Commercial Product 5 | Liquid | No |
| Commercial Product 6 | Liquid | No |
| Commercial Product 7 | Gel | No |
| Commercial Product 8 | Liquid | No |
| Commercial Product 9 | Liquid | No |
| Commercial Product 10 | Liquid | No |
| Commercial Product 11 | Liquid | No |
| Commercial Product 12 | Liquid | No |
| Commercial Product 13 | Liquid | No |
| Commercial Product 14 | Liquid | No |
| Example 1 | Liquid | Yes |
| Example 2 | Liquid | Yes |

*Sprayable composition denotes a filled pattern upon the target area.
Commercial Product 1: K-Y ® Liquid ™ (Personal Products, Skillman, N.J.)
Commercial Product 2: K-Y ® Ultragel ™ (Personal Products, Skillman, N.J.)
Commercial Product 3: Astroglide (BioFilm, Inc., Vista, CA.)
Commercial Product 4: WET Original (WET Formula International, North Hollywood, CA.)
Commercial Product 5: WET Light (WET Formula International, North Hollywood, CA.)
Commercial Product 6: ForPlay (Trimensa Pharmaceuticals, Newbury Park, CA.)
Commercial Product 7: Vagisil Intimate Moisturizer (COMBE Incorporated, White Plains, N.Y.)
Commercial Product 8: Aqua Lube (Mayer Laboratories, Inc., Oakland, CA.)
Commercial Product 9: PROBE (Davryan Laboratories, Inc., Portland, OR.)
Commercial Product 10: EROS (CDC Distribtion Center, Fleishstraube, Germany)
Commercial Product 11: play (Durex Consumer Products, Inc., Norcross, GA.)
Commercial Product 12: SYLK (Geneva Marketing, Auckland, New Zealand)
Commercial Product 13: TROJAN Crystal Clear Liquid (Church & Dwight Co., Inc., Princeton, N.J.)
Commercial Product 14: I-D (Westridge Laboratories, Inc., Newport Beach, CA.)

As shown by the results set forth in Table 1, there are no commercially available lubricant products that deliver the lubricant in a filled pattern upon the target area.

What is claimed is:

1. A method of providing personal lubrication comprising (a) placing a sprayable anhydrous personal lubricant composition for application to the skin or mucous membranes of a mammal in a swirl chamber pump spray mechanism and (b) dispensing said composition as a target spray to a target area from a distance of, wherein the sprayable anhydrous personal lubricant composition for application to the skin or mucous membranes of a mammal has a warming effect when so applied and consists essentially of at least 50% by weight of propylene glycol and at least one polyethylene glycol wherein the composition has a viscosity less than about 250 cps and a lubricity of at least 8 as determined by the Ahmad procedure, is lubricious, and upon spraying from a swirl chamber pump spray mechanism, the composition is atomized into particles having a particle size distribution at a 3" spray distance of at least about 400 μm in the $10^{th}$ percentile, at least about 40 μm in the $50^{th}$ percentile and at least about 100 μm in the $90^{th}$ percentile and at 6", at least about 200 μm in the $10^{th}$ percentile, at least about 40 μm in the $50^{th}$ percentile and at least about 75 μm in the $90^{th}$ percentile.

2. A method of providing personal lubrication in accordance with claim 1 wherein the viscosity of the composition is from about 10 to about 150 cps.

3. A method of providing personal lubrication in accordance with claim 1 wherein the polyethylene glycol has repeating ethylene glycol units of about 300 to about 1450.

4. A method of providing personal lubrication in accordance with claim 1 wherein said swirl chamber pump spray mechanism dispenses said composition in a conical-shaped pattern.

5. A method of providing personal lubrication in accordance with claim 1 wherein said composition consists essentially of (a) a compound selected from the group consisting of polyethylene glycol 400, polyethylene glycol 1000, polyethylene glycol 1450 or a mixture thereof; and (b) propylene glycol.

* * * * *